(12) United States Patent
Wang et al.

(10) Patent No.: US 6,693,166 B1
(45) Date of Patent: *Feb. 17, 2004

(54) CDK5—SPECIFIC INHIBITORY PEPTIDES

(75) Inventors: Jerry H. Wang, Kowloon (HK); Mingjie Zhang, Kowloon (HK); Damu Tang, Kowloon (HK)

(73) Assignee: Hong Kong University of Science and Technology, Hong Kong (HK)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/289,612

(22) Filed: Apr. 12, 1999

(51) Int. Cl.[7] .............................................. A61K 38/00
(52) U.S. Cl. ...................... 530/324; 530/326; 530/350; 514/2; 514/12; 514/13
(58) Field of Search ............................... 514/2, 12, 13; 530/324, 326, 350

(56) References Cited

PUBLICATIONS

Ngo et al., 'Computational Complexity, Potein Structure Prediction, and the Levinthal Paradox,' The Protein Folding Problem and Tertiary Structuer Prediction. Ed. K. Merz and L. Le Grand. BirkHauser, Boston MA, pp. 491–495, 1994.*
Rudinger, J. (1976). Peptide Hormones (ed. J.A. Parsons). University Park Press. Baltimore. pp 1–7, 1976.*
Tang et al. 'Cyclin–dependent kinase 5 (Cdk5) activation domain of neuronal Cdk5 activator. Evidence of the existence of cyclin fold in neuronal Cdk5a activator', J. Biol. Chem. (1997), 272(19), 12318–12327, May 1997.*
Tsai et al. 'P35 is a neural–specific regulatory subunit of cyclin–dependent kinase 5,' Nature (London) (1994), 371(6496), 419–23.*
Patel et al. 'Pharmacotherapy of Cognative Impairment in Alzheimer's Disease: A Review', J. Geriatr. Psychiatry Neurol. vol. 8, 1995, pp. 81–92*

* cited by examiner

Primary Examiner—Brenda Brumback
Assistant Examiner—Anish Gupta
(74) Attorney, Agent, or Firm—Baker & McKenzie

(57) ABSTRACT

The activation of cyclin dependent kinase 5 (Cdk5) depends on the binding of its neuronal specific activator Nck5a. The minimal activation domain of Nck5a has been experimentally determine comprise acid residues 150 to 291 of the protein. It has been demonstrated that a 28 residue peptide encompassing amino acid residues Ala 146 to Asp 173 of Nck5a is capable of binding Cdk5 and hence resulting in the inhibition of its Kinase activity. Additionally, this peptide could also inhibit Cdk2 with a similar potency as it does to Cdk5. The direct competition experiments showed that the Nck5a inhibitory peptide does not compete with Nck5a for Cdk5 or cyclin A for Cdk2. Steady state kinetic analysis indicated that the Nck5a peptide acts as a non-competitive inhibitor of Cdk5/Nck5a complex with respect to its substrate. The structure of the peptide in solution as determined by the methods of circular dichroism and two-dimensional 1H NMR spectroscopy have been performed in order to understand the molecular basis of kinase inhibition by the peptide. A segment of the peptide, corresponding to amino acid resides Ser149 to Arg169 adopts an amphipathic alpha-helical structure in solution. Four Leu residues and one Phe residue clustered on the hydrophobic face of the helix, and this hydrophobic face is likely to be the contact area when the peptide binds and inhibits both Cdk5 and Cdk2. Mutational experiments have also indicated that the C-terminal end of the peptide contributes to the inhibition of Cdk5 and Cdk2.

5 Claims, 10 Drawing Sheets

FIG. 1

```
                         αN-term
             177                                              207
CyclinA      DYHE DIHTYLREME VKCKPKVGYM KKQPDIT
Nck5a        ASTS ELLRCLGEFL CRRCYRLKHL S.PTD
             146  ••••••••••••••••••••••••••  173
```

CDK5— SPECIFIC INHIBITORY PEPTIDES

BACKGROUND OF THE INVENTION

1) Field of Invention

The present invention relates to cyclin-dependent kinase (Cdk) inhibiting peptides that have specific inhibition effect on certain cyclin-dependent kinases. Cdks are key regulatory enzymes in the eukaryotic cell cycle.

2) Description of Prior Art

Cyclin-dependent kinases (Cdks) are key regulatory enzymes in the eukaryotic cell cycle. The activation of a Cdk depends on its association with its specific cyclin partner. The activity of these enzymes is further regulated by an intricate system of protein-protein interactions and phosphorylation (Morgan, D. O., 1995). Members of the Cdk family are closely related by sharing a high level of amino acid sequence identity (40%–70%). In contrast, cyclins are a family of molecules of diverse molecular mass and low sequence identity. Sequence alignments have shown that cyclins share a conserved region of approximately 100 amino acids in the center of the molecule, and this region is called the cyclin box. Recent crystal structures of cyclin A and cyclin H have shown that the cyclin box sequence forms a compact five-helix domain called the cyclin fold. The C-terminal domain of cyclin A also forms the cyclin fold, although there is virtually no sequence similarity between the two cyclin domains. Theoretical predictions have suggested that, like cyclin A, other members of the cyclins also contain two cyclin folds.

Unlike other Cdks, Cdk5 activity has been observed only in neuronal and developing muscle cells although the catalytic subunit of the enzyme is present in many mammalian tissues and cell extracts. Recent experimental evidence has demonstrated that Cdk5 plays important roles in neurite outgrowth, patterning of cortex and cerebellum, and cytoskeletal dynamics. Loss of regulation of Cdk5 has been suggested to be involved in Alzheimer's disease (Lew, J and Wang. J. H., 1995). Active Cdk5 was first purified from brain extract as a heterodimer with subunit molecular masses of 33- and 25-kDa. The 33-kDa subunit was later identified as Cdk5, and the 25-kDa activator (Neuronal Cdk5 activator, Nck5a) was a novel protein with no sequence similarity to any other proteins. The 25-kDa subunit was later found to be proteolytic product of a larger 35-kDa protein. An isoform of Nck5a (Nck5ai) with 57% sequence identity to Nck5a has also been identified. Despite their functional similarity (i.e.: binding and activation of a Cdk), the Cdk5 activators share little sequence similarity to cyclins. Moreover, activation of Cdk5 is independent of phosphorylation of Cdk5 at Ser195 by Cdk activating kinase, CAK. Recently, the activation domain of Nck5a was precisely mapped to the amino acid residues from Glu149 to Asn291. Extensive truncation and site-directed mutation studies of Nck5a, together with computer modelling, strongly suggested that the 142-residue activation domain of Nck5a adopt a cyclin fold structure.

All currently known peptides that have regulatory effects on Cdk5 and Cdk2 are usually ATP/ADP-based. The disadvantages of ATP/ADP-based peptides include their low efficiency of their binding. In addition, they bind to Cdks with low specificity.

OBJECTION OF THE INVENTION

It is an object of the present invention to provide potent Cdk5/Cdk2 specific inhibitory peptides. In particular, it is the object of the present invention to identify the critical binding characteristics of the peptide fragments of Nck5a.

SUMMARY OF INVENTION

Cyclin-dependent Kinases (Cdks) are key regulatory enzymes in the eukaryotic cell cycles. The activation of a Cdk depends on its associating with its specific cyclin partner. In the case of Cdk5, its activation has been shown to occur upon the binding of Nck5a (neuronal Cdk5 activator). A 28-residue peptide encompassing amino acid residues Ala 146 to Asp 173 of Nck5a was discovered to be able to bind to Cdk5 and hence result in kinase inhibition. Additionally, it is found that this peptide could inhibit Cdk2 with an even higher potency than its inhibition of Cdk5. This Nck5a-derived peptide was able to inhibit Cdk5 both during and after reconstitution of the enzyme with Nck5a, suggesting that the peptide does not directly compete with Nck5a for Cdk5. The addition of a 1000-fold excess of the synthetic peptide does not lead to the dissociation of Nck5a from Cdk5 or cyclin A from Cdk2. To identify the molecular basis of kinase inhibition by the peptide, the structure of the peptide in solution was determined by the methods of circular dichrosim and two-dimensional $^1$H NMR spectroscopy. The peptide segment adopts an amphiphilic alpha-helical structure from residues Ser149 to Arg162. Four Leu residues and one Phe residue clustered on the hydrophobic face of the helix, and this hydrophobic phase is likely to be the contact area when the peptide binds to Cdk5 and Cdk2. Additionally, a number of peptide analogs were generated, and their inhibitory capacities were also measured. The peptides discovered in this work serve as bio-medical reagents as well as leads for novel drug discovery.

The present invention relates to the identification and characterisation of a 29-residue Cdk inhibitory peptide, which is derived from an internal fragment of Nck5a. This peptide is able to bind to and hence inhibit the Cdk5/Nck5a and Cdk2/cyclinA complexes in a non-competitive manner. The solution structure of the peptide determined by two-dimensional NMR spectroscopy showed that a large part of the peptide adopts an amphipathic alpha-helical structure, and that this helix is likely to be the main contacting area of the peptide that interacts with the enzyme complex.

This Nck5a-derived peptide is the first reported inhibitory peptide of Cdk5. As a result, of the peptides inhibitory specificities against Cdk5 and Cdk2 this peptide possess important and valuable implications as a scientific tool to support biomedical research in cell cycle regulation. These peptides may also be further developed into potential drugs targeting Cdk5/Cdk2 inactivation. Furthermore, the Nck5a-derived peptide possess immediate utility as bio-medical research tools. This peptide can also serve as leads for the development of novel drugs targeting the inhibition of both Cdk5 and Cdk2.

BRIEF DESCRIPTION OF THE DRAWINGS

FIG. 1:

Figure 2:
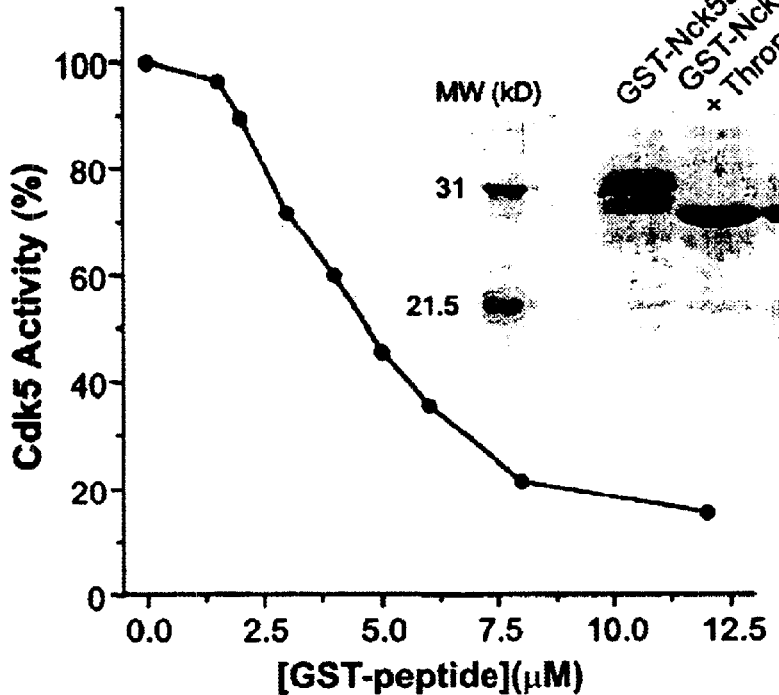
Figure 2:
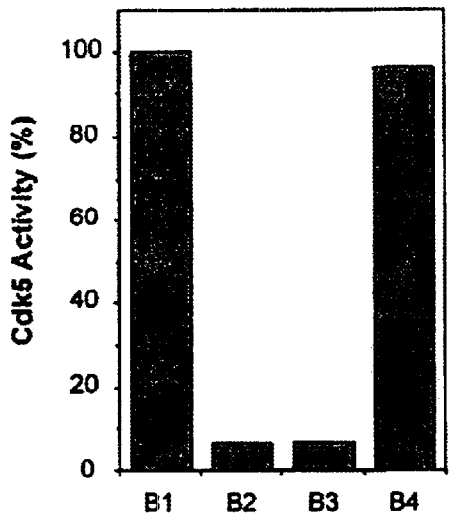
Figure 2:
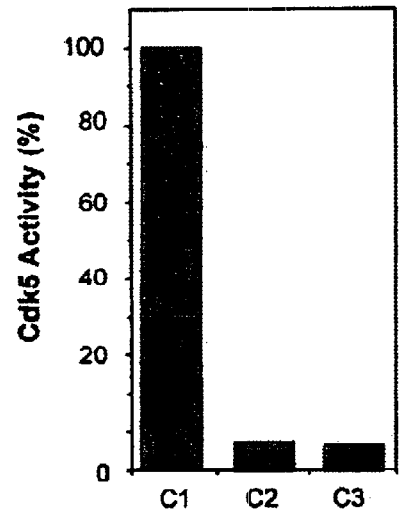

Amino acids sequences of the synthetic Nck5a (SEQ ID NO:1) peptide and the cyclin A peptide (SEQ ID NO:4) used in this work. The alignment of two peptide sequences was derived by aligning cyclin A and the minimal activation domain of Nck5a. The black bar above the cyclin A peptide represents the N-terminal alpha-helix of the protein found in the X-ray structure. The dotted region (SEQ ID NO:2) below the Nck5a peptide depicts the predicted alpha-helix of the peptide.

FIG. 2:

Discovery and inhibitory properties of the Nck5a peptide

A. Dose-dependent inhibition of Cdk5 by the bacterially expressed GST-fused Nck5a peptide. The insert SDS-PAGE data show the purified GST-Nck5ap, and its thrombin digestion product as well as GST. The mirror bands seen in the lane of GST-Nck5ap were due to proteolytic degradation of the GST-fusion peptide since the cleavage of the fusion peptide by thrombin resulted in the production of only one band which corresponds to GST.

B. Reconstituted GST-Cdk5-GST-Nck5ap kinase activity (B1), and its inhibition by GST-Nck5ap (B2), the Nck5a peptide released by the addition of thrombin (B3), and by GST as a control (B4).

C. Inhibition of Cdk5 by the Nck5a peptide both before and after its reconstitution with Nck5a. The addition of the GST-Nck5a peptide to GST-Cdk5 before [GST-Cdk5+GST-p25+GST-Nck5ap; C2] or after (GST-Cdk5/GST-p25+GST-Nck5ap; C3] its reconstitution with GST-p25 resulted in the same kinase activity inhibition. C1 serves as a positively control of Cdk5 activity.

FIG. 3:

Dose dependent inhibition of (A), Cdk5 and (B), Cdk2 by various concentrations of the synthetic Nck5a peptide. The negative control peptide was derived from residues 6 to 20 of Cdc2 with an alanine to serine substitution at position 14. The cyclin A peptide encompasses the N-terminal alpha-helix of cyclin A, and was used to assess the specificity of the corresponding Nck5a peptide. The MLCK peptide corresponds to the calmodulin-binding domain of skeketal myosin light chain kinase.

FIG. 4:

The Nck5a peptide acts as a noncompetitive inhibitor with respect to Cdk activators.

A. Increasing amounts of the Nck5a peptide (Lane 1 to 4: 0, 5, 20, 50 $\mu$M, which corresponded to 05, 105, 50% and 90% inhibition of Cdk5 activity, respectively) were incubated with GSH-agarose beads, and the amount of complex remaining was assayed by immunoblotting of Cdk5. Lane 5: without adding peptide, similar amount of GST was used instead of GST-p25 as a negative control for binding to H6-Cdk5.

B. Increasing amounts of the Nck5a peptide (Lane 1 to 4: 0, 0.5, 2, 10 $\mu$M, which corresponded to 0%, 10%, 50% and 90% inhibition of Cdk2 activity, respectively) were incubated with the GST-Cdk2/Cyclin A-His6 complex. The GST-Cdk2/cyclin. A-His6 complex was precipitated by GSH-agarose beads. The remaining amount of complex was measured by Western blot of Cyclin A-H6. Again, GST instead of GST-Cdk2 was used as negative control for binding to Cyclin A-H6 (lane 5).

FIG. 5:

Increase in p25$^{nck5a}$ cannot decrease Cdk5 inhibition by Nck5a peptide: Different amounts of GST-p25$^{nck5a}$ (2, 20, 40 $\mu$g) were reconstituted with 1 $\mu$g GST-Cdk5 and assay for Histone H1 peptide activity without (■) or with (□) 50 uM Nck5a peptide at which give an approximate 90% inhibition.

FIG. 6:

Steady state kinetic analysis of Cdk5 inhibition by Nck5a peptide.

A. Concentration dependent inhibition of Cdk5 activity by the Nck5a peptide. the data were fitted by "Sigmoidal fitting" function using "Microcal™ Origin™ 4.1" (Microcal Software, Inc.).

B. Double Reciprocal plot of the Nck5a peptide inhibition of the Cdk5/Nck5a complex. Four different concentrations of $\mu$M the Nck5a peptide were used in the assay [0 $\mu$M (●), 10 $\mu$M (▲), 20 $\mu$M (■), 30 $\mu$M (▼)]. The data were fitted by standard linear least square fitting.

C. Dixon plot of Nck5a peptide inhibition of Cdk5. The concentrations of the Histone H1 peptide used were: 7.5 $\mu$M (○), 10 $\mu$M (Δ), 15 $\mu$M (□), 30 $\mu$M (▽).

FIG. 7:

Ultraviolet CD spectra of the Nck5a peptide (50 $\mu$M) in various concentration of TFE (0%, 5%, 10%, 15%, 20%, and 30%, respectively) at 35° C., pH 4.0. The insert shows the change ellipticity at 222 nm as a function of TFE concentration.

FIG. 8:

Amide-amide region of the NOESY spectrum (mixing time=150 msec) of the Nck5a peptide dissolved in 30% (v/v) TFE/H$_2$O at 35° C. A number of strong and continuous (i, i+1) NOEs are observed and corresponding labelled in the spectrum.

FIG. 9:

Summary of the NOE connectivities of the Nck5a peptide in 30% (v/v) TFE aqueous solution. NOEs were derived from NOESY spectra in both TFE/H2O and TFE/D2O mixtures. The height of the boxes indicates the relative intensity of the NOE crosspeaks. The dashed lines indicate the relative intensity of the NOE crosspeaks. The dashed lines indicate the NOEs that are ambiguous due to resonance overlap. Chemical shift index (CSI) data of the alpha protons are also include in the figure.

FIG. 10:

Helical wheel presentation of the Nck5a peptide structure in 30% TFE/H$_2$O derived from NMR data. The hydrophobic and hydrophilic faces of the peptide are separated by a dashed line for clarity.

DETAILED DESCRIPTION OF THE INVENTION

The present invention comprises the identification of specialised regions in Nck5a in which specific regulatory functions are manifested. In particular, two specific regions on Nck5a are identified to be able to specifically and discriminatively inhibit Cdk5 and Cdk2. The major difference between existing known Cdk regulatory enzymes and the presently identified fragments of Nck5a peptide is that Nck5a peptide has a much higher efficiency and specificity. The following experiments illustrate the characteristics and specificity of several internal fragments of Nck5a.

Peptide Synthesis—A 28-residue peptide (ASTSELLRCLGEFLCRRCYRLKHLSPTD) (SEQ ID NO:1) corresponding to peptide fragment Ala$^{146}$ to Asp$^{173}$ of Nck5a was synthesised on an Applied Biosystems Model A431 automated peptide synthesizer using Fmoc-based chemistry (FIG. 1). A 31-residue peptide (DYHDIHTYLREMEVKPKPKVGYMKKQPDIT) (SEQ ID NO:5) corresponding to the sequence Asp177 to Thr207 of human cyclin A was synthesized in the same manner (FIG. 1). After cleavage from the solid support, the peptides were purified by gel filtration and reverse phase high performance liquid chromatography to a purity greater than 95%. All of the peptide purifications were carried out in 0.1% trifluoroacetic acid/H$_2$O (v/v) as low pH can prevent the oxidation of the sulfhydryl group of the Cys residues in the peptides. Trifluoroacetic acid was removed from the peptide by dissolving the lyophilized peptide powder in pre-chilled Milli-Q water before re-lyophilization. The authenticity of the peptides was checked using mass spectrometry as described above.

Protein Expression and Purification—GST-Cdk5 and GST-Nck5a were prepared as described previously. The N-terminal histidine-tagged Cdk5 (H6-Cdk5) was expressed in and purified from *Escherichia Coli* cells (strain M15 from Qiagen). The host cells, harboring a H6-Cdk5-containing expression plasmid, were cultured in 6 liters of tryptone/phosphate-rich medium containing 50 µg/ml of ampicillin and 25 µg/ml kanamycin to $A_{600} \approx 1.0$ before induction of protein expression with isopropyl-1-thio-β-D-galactopyranoside (0.4 mM). The cell culture was subsequently incubated for 10 h at 22° C. The pelleted cells were washed with 20 mM Tris-HCl, pH 7.5, containing 1 mM EDTA. Cells were then lysed in 50 mM Tris-HCl buffer, pH 7.5 using a French press, and the lysate was subjected to centrifugation at 38,700×g for 30 min. The pH of the resulting supernatant was adjusted to 7.9, and this was then incubated with 3 ml of $Ni^{2+}$-nitrilotriacetic acid-agarose ($Ni^{2+}$-NTA) beads for 1 h with stirring. The resin was packed onto a column and then washed with 50 ml of binding buffer (20 mM Tris-HCl, pH 7.9, 0.5 M NaCl, 5 mM imidazole) and 30 ml of washing buffer (20 mM Tris-HCl, pH 7.9, 0.5 M NaCl, 60 mM imidazole). H6-Cdk5 was then eluted with about 18 ml of elution buffer (20 mM Tris-HCl, pH 7.9, 1 M NaCl, and 1 M imidazole).

The C-terminal histidine-tagged human cyclin A (cyclin A-H6) was expressed and purified in essentially the same manner as described for H6-Cdk5. Briefly, the expression plasmid pET21d containing a cyclin A gene lacking the N-terminal 173 amino acids was transformed into BL21 (DE3) *E. coli* cells. The host cells were cultured in LB medium containing 100 µg/ml ampicillin, and cyclin A expression was induced by adding isopropyl-1-thio-β-D-galactopyranoside to a final concentration of 0.1 mM. The induction of cyclin A expression was for 3 h at 30° C. The pelleted cells were resuspended in 50 mM Tris-HCl, pH 7.5, 300 mM NaCl, and 0.05% Triton X-100, and then lysed in the French press. The subsequent purification of cyclin A using a $Ni^{2+}$-NTA column was carried out in a manner identical to that described for the purification of H6-Cdk5. The monomeric, active form of cyclin A-H6 was further purified by passing the cyclin A-H6-containing eluent through a Sephacryl S-200 gel filtration column (Amersham Pharmacia Biotech).

Peptide/Cdk Binding Assay—H6-Cdk5 (about 3 µg) and 15 µg of GST-p25 were premixed in 300 µl of 1×phosphate-buffered saline with 0.5 mg/ml bovine serum albumin. Some 50-µl quantities of the mixture was taken out to mix with various concentrations of the $\alpha_N$ peptide (from serial dilutions made from a 2.0 mM stock solution), and the total volume of the mixture was adjusted to 150 µl using Buffer R (1×phosphate-buffered saline containing 1 mM EDTA, 1 mM dithiothreitol, 0.6 mM phenylmethylsulfonyl fluoride, 1 µg/ml leupeptin, 1 µg/ml leupeptin, 1 µg/ml antipain, 5 mg/ml bovine serum albumin). The reaction mixture was incubated at 4° C for 15 h. GST-Nck5a-H6-Cdk5 complex was then precipitated by the addition of 40 µl of GSH-Sepharose beads pre-equilibrated with 1×phosphate-buffered saline (50%, v/v). The GSH-Sepharose beads were washed three times with 1×phosphate-buffered saline buffer, and subsequently resuspended in 20 µl of water and 20 µl of 2×protein sample treatment buffer. The co-precipitated H6-Cdk5 was detected by SDS-PAGE followed by Western blot using a monoclonal antibody against Cdk5.

The binding of the $\alpha_N$ peptide to the GST-Cdk2-cyclin A-H6 complex was studied in a similar manner to that described above for H6-Cdk5. Briefly, 3 µg of GST-Cdk2 and 10 µg of cyclin A-H6 were reconstituted in Buffer R with various concentrations of the $\alpha_N$ peptide at 4° C. for 15 h. GST-Cdk2 was then precipitated by the addition of 20 µl of GSH-Sepharose beads. After washing, the co-precipitated cyclin A-H6 was detected by SDS-PAGE followed by Western blot using a monoclonal antibody against cyclin A (Santa Cruz).

Peptide Inhibition of Cdk5 and Cdk2 Kinase Activity—Cdk5 kinase activity was assayed essentially as described previously, except that for each Cdk5 kinase reaction 1 µg of GST-Cdk5 was reconstituted with 2 µg of GST-Nck5a, and 1 µg of GST-Cdk2 was mixed with 3 µg of cyclin A-H6 in Cdk2 assays. The reconstituted complexes were added, in duplicate, to an assay mixture containing 30 mM MOPS, pH 7.4, 10 mM $MgCl_2$, 40 µM of the histone H1 peptide, 50 µM [$\gamma$-$^{32}$P]ATP, and various concentrations of various peptides at 30° C. for 30 min before measuring the Cdk5 and Cdk2 kinase activities.

Steady State Kinetic Experiments—All assay conditions were the same as in the inhibition assay described above, except that the reaction time was kept at 15 min so that the product formed was less than 5% of the total substrate concentration used. To determine suitable concentrations of the substrate and the inhibitor for the steady state kinetic experiments, the $K_m$ value of GST-Cdk5.GST-Nck5a complex and a concentration-dependent inhibition profile of the enzyme by the $\alpha_N$ peptide were determined. Four different concentrations of the histone H1 peptide (7.5, 10, 15, and 30 µM) were used in the kinetic analysis of the enzyme inhibition. For each substrate concentration, four concentrations of the $\alpha_N$ peptide (0, 10, 20, and 30 µM) were used in the inhibition assay.

CD Experiments—Concentrations of the $\alpha_N$ peptide stock solutions were determined by the UV absorption of the single Tyr residue at 280 nm. For CD measurement, the $\alpha_N$ peptide was dissolved in a 20 mM sodium acetate buffer, pH 4.0, containing various concentrations of 2,2,2-trifluoroethanol (TFE). The concentration of the peptide was fixed at 50 µM throughout the experiment. CD spectra were collected at 35° C. on a JASCO J-720 CD spectropolarimeter equipped with a Neslab temperature controller using a cell path length of 1 mm.

NMR Experiments—For NMR studies, the $\alpha_N$ peptide was dissolved in unbuffered 90% $H_2O$, 10% $D_2O$, or 99.99% $D_2O$ containing various concentrations of deuterated TFE-$d_3$ (0~30%, v/v), and 2 mM deuterated dithiothreitol-$d_{10}$ at pH (or pD) 4.0. The concentration of the $\alpha_N$ peptide was approximately 2.0 mM. All $^1$H NMR data were recorded on a Varian INOVA 500 spectrometer at a $^1$H frequency of 500.11 MHz. Two-dimensional TOCSY and NOESY spectra were acquired with a spectral width of 6000 Hz in both dimensions (24). The "WET" pulse sequence was employed for solvent suppression (Bax, A, 1985) of the peptide samples in $H_2O$. FID data matrices were composed of 512×2048 ($t_1 \times t_2$) data points. The mixing times used in NOESY experiments were 150 and 300 ms. TOCSY spectra were recorded with a mixing time of 75 ms using the MLEV17 spin lock sequence. All NMR data were processed and displayed using the nmrPipe software package.

Results

A Peptide Derived from the N-terrminal Region of the Activation Domain of Nck5a Inhibits the Kinase Activity of Cdk5 and Cdk2—In the course of studying the structure and function relationship of the activation domain of Nck5a, we created a series of truncated forms of GST-Nck5a mutants. One such GST fusion mutant, which contains a 29-residue peptide fragment corresponding to residues Gln$^{145}$ to Asp$^{173}$ of Nck5a (termed $\alpha_N$ as it represents the N-terminal α-helix of Nck5a, see "Discussion") was found to inhibit Cdk5 kinase activity in a dose-dependent manner (FIG. 2A). About 50% kinase activity was inhibited at a GST-$\alpha_N$ concentration of 5 μM. The inhibition of Cdk5 activity originated solely from the peptide fragment as GST did not have any effect on the kinase activity of the enzyme (FIG. 2B). Release of the peptide from the fusion protein by thrombin had no effect on the inhibitory activity (FIG. 2B). Furthermore, the addition of GST-$\alpha_N$ before or after the reconstitution of GST-Cdk5 with GST-Nck5a gave rise to the same inhibition profiles (FIG. 2C), suggesting that the peptide does not compete with Nck5a for Cdk5 (see below for more details). We also tested the inhibitory effect of GST-$\alpha_N$ toward the GST-Cdk2.cyclin A-H6 complex, and found that GST-$\alpha_N$ also inhibited the kinase activity of Cdk2. As expected, the inhibition of the Cdk2.cyclin A complex originated from the $\alpha_N$ peptide portion of the fusion protein, as seen in the case of Cdk5 (data not shown, see below for results obtained with the synthetic peptide).

Low expression level (about 1 mg/ml of soluble GST-$\alpha_N$) and poor homogeneity of the GST fusion product prevented us from a detailed characterization of this inhibitory peptide. To overcome these problems, we decided to use a synthetic peptide instead of the GST fusion protein. A 28-residue peptide (SEQ ID NO:1) corresponding to amino acid residues Ala$^{146}$ to Asp$^{173}$ of Nck5a (abbreviated as the $\alpha_N$ peptide) was synthesized and purified to homogeneity. The N-terminal Gln residue (Gln$^{145}$) was deleted from the synthetic peptide sequence to avoid complication from its cyclization to form gyroglutamate. The titration curves shown in FIGS. 2 and 3A revealed that both the recombinant and synthetic inhibitory peptides inhibit GST-Cdk5.GST-Nck5a complex with similar potencies.

Figure 3:
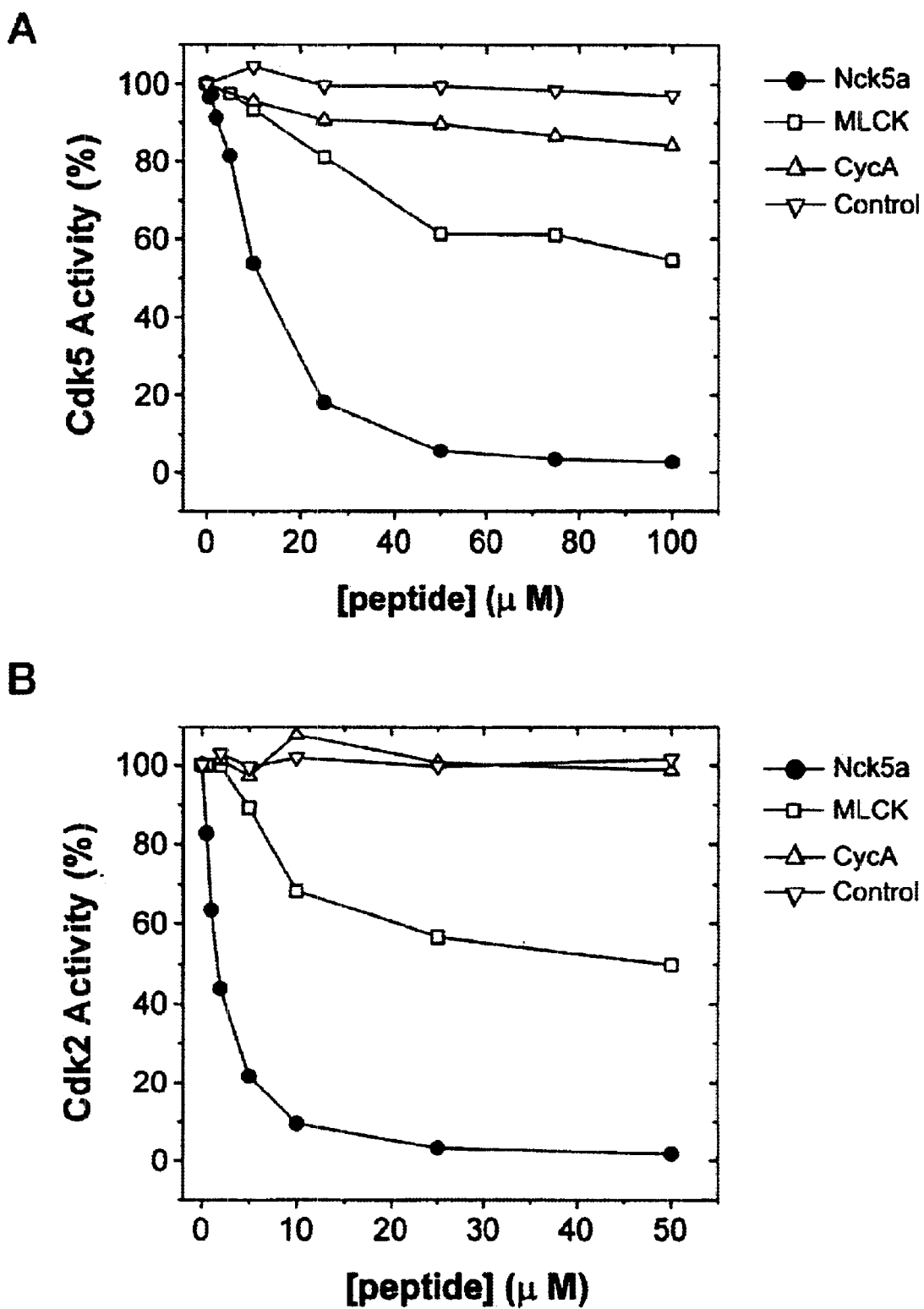

In order to assess whether the $\alpha_N$ peptide was a specific inhibitor of Cdk5 and Cdk2, we synthesized a 31-residue peptide (SEQ ID NO:4) corresponding to Asp$^{177}$ to Thr$^{207}$ of cyclin A (the cyclin A peptide, FIG. 1), and tested for its ability to inhibit GST-Cdk5.GST-Nck5a. This region of cyclin A was previously shown to align with the $\alpha_N$ peptide based on the sequences, the secondary structures, and the functions of the two proteins (Cheng, H.-C, 1996). Despite the fact that the cyclin A peptide could adopt an α-helical conformation similar to that seen in its crystal structure, the cyclin A peptide inhibited neither GST-Cdk5.GST-Nck5a nor GST-Cdk2.cyclin A-H6 (FIG. 3). Therefore, it is likely that the unique amino acid sequence of the $\alpha_N$ peptide entails its inhibition of Cdk5 and Cdk2.

Additionally, the $\alpha_N$ peptide was shown to adopt an amphipathic α-helical structure in solution (see below), we tested the Cdk inhibitory effect of another amphipathic peptide, a 26-residue peptide fragment comprising the calmodulin-binding domain of myosin light kinase (the MLCK peptide). Although MLCK peptide was indeed able to inhibit the activities of GST-Cdk5.GST-Nck5a and GST-Cdk2.cyclin A-H6, its inhibitory efficiency is significantly lower than that of the $\alpha_N$ peptide (FIG. 3). Therefore, it is suggested that the potent and efficient inhibitory activity of the $\alpha_N$ peptide is due to the unique amino acid sequence.

Figure 4:
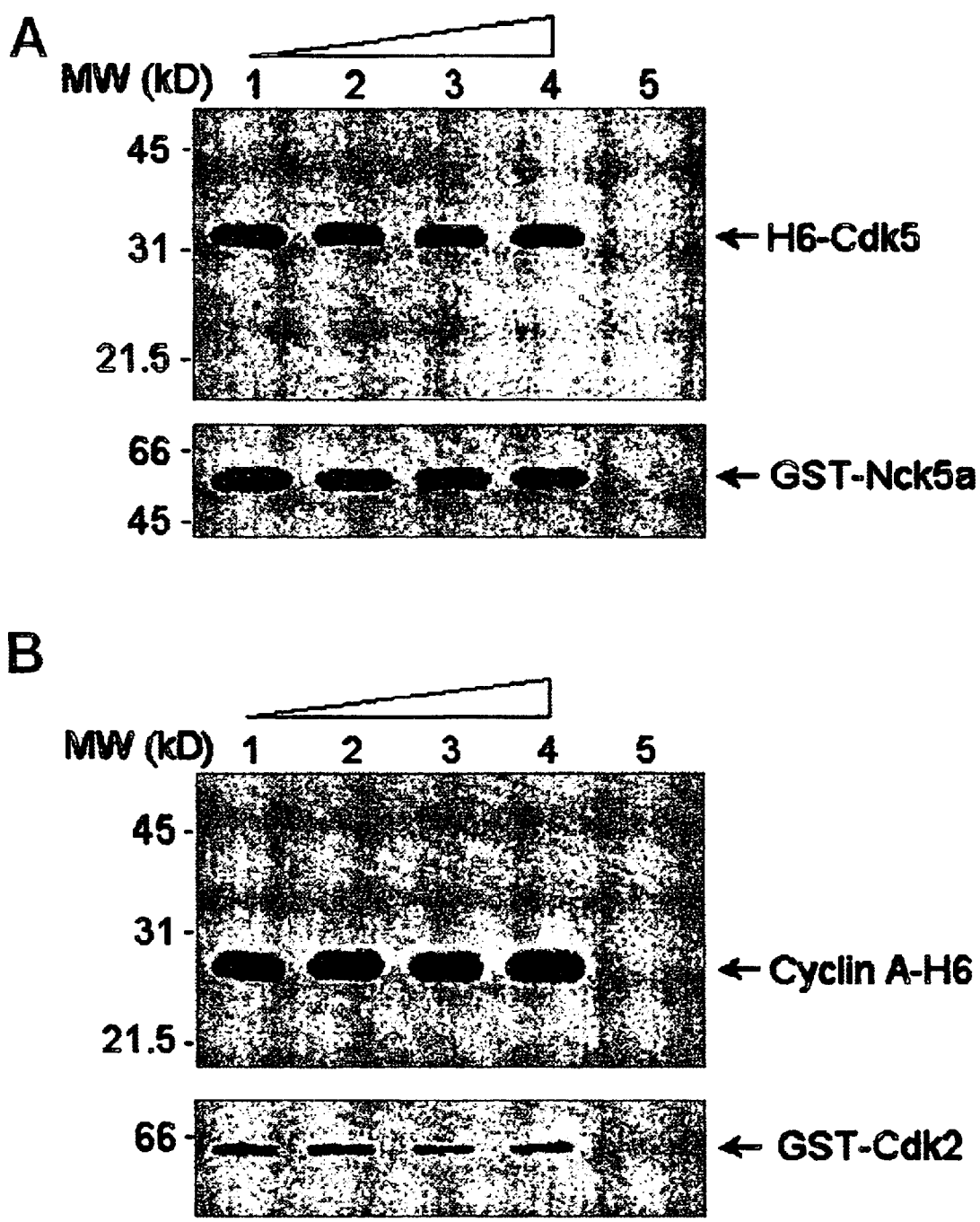

The Binding of the $\alpha_N$ Peptide to Cdk5.Nck5a and Cdk2.Cyclin A Complexes Does Not Lead to a Dissociation of Nck5a and Cyclin A—The inhibition of Cdk5 and Cdk2 by the $\alpha_N$ peptide shown in FIG. 3 may result from a direct competition of the peptide with GST-Nck5a and Cyclin A-H6 for GST-Cdk5 and GST-Cdk2, respectively, or from the binding of the peptide to the binary complexes of GST-Cdk5.GST-Nck5a and GST-Cdk2.cyclin A-H6. To discriminate between these possibilities, we performed direct binding competition experiments. Various concentrations of the peptides were added to a H6-Cdk5.GST-Nck5a mixture, and GST-Nck5a was then precipitated using GSH-agarose beads. The amount of H6-Cdk5 in complex with GST-Nck5a was determined by Western blotting of the enzyme co-precipitated by GSH-agarose beads. The amount of H6-Cdk5 and cyclin A-H6 used in the experiment described in FIG. 4, A and B, were chosen to ensure that their respective antibodies would be in excess. The addition of various amounts of the $\alpha_N$ peptide (corresponding to approximately 10, 50, and 90% inhibition of the Cdk5 activity) did not lead to a dissociation of GST-Nck5a from H6-Cdk5 (FIG. 4A), indicating that the $\alpha_N$ peptide was able to bind to and hence inhibit the binary complex of H6-Cdk5.GST-Nck5a. Similarly, the inhibition of GST-Cdk2.cyclin A-H6 activity by the $\alpha_N$ peptide also resulted from the formation of a ternary complex between the $\alpha_N$ peptide and GST-Cdk2.cyclin A-H6 rather than from a direct competition between the $\alpha_N$ peptide and cyclin A for Cdk2 (FIG. 4B). The activity of the Cdk5.Nck5a complex could be inhibited immediately upon the addition of the $\alpha_N$ peptide (FIG. 2C), further indicating that the $\alpha_N$ peptide can bind to and inhibit Cdk5 without the dissociation of its activator.

Figure 5:
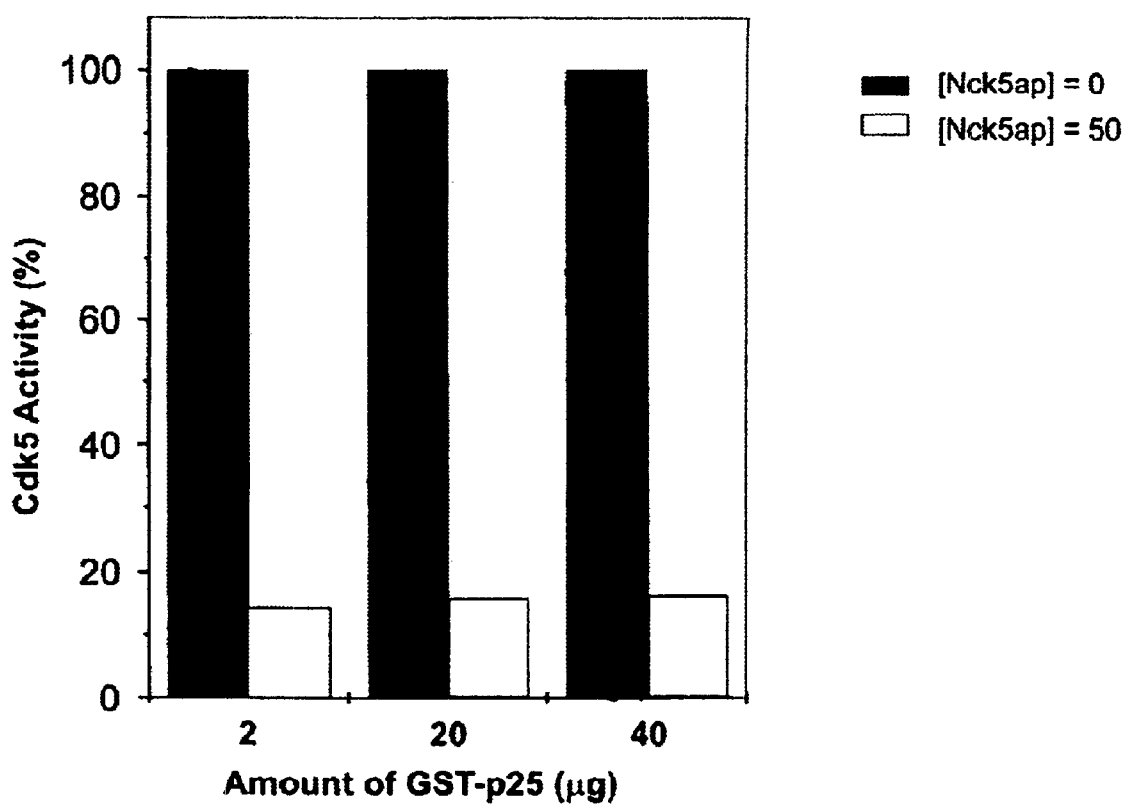

To further prove that the $\alpha_N$ peptide does not complete with Nck5a for Cdk5, we performed a direct competition experiment. First, GST-Cdk5 was reconstituted with various concentrations of its activator. Then, we assayed the inhibition of the reconstituted GST-Cdk5.GST-Nck5a complexes by the $\alpha_N$ peptide (50 μM, a concentration which leads to about 90% inhibition of the enzyme, see FIG. 3). If the inhibitory peptide were to compete with Nck5a for Cdk5, the large excess of Nck5a would mask the inhibition of the kinase by the peptide at low concentrations. However, data in FIG. 5 show that the presence of a large excess of GST-Nck5a has no significant effect on the enzyme inhibition profile by the $\alpha_N$ peptide, further supporting the contention that the inhibitory peptide does not compete with Nck5a for Cdk5.

Kinetic Analysis of Cdk5 Inhibition by the $\alpha_N$ Peptide—We also analyzed the kinetic properties of the $\alpha_N$ peptide with respect to the kinase substrate, the histone H1 peptide. The double-reciprocal plot shown in FIG. 6A demonstrates that the peptide acts as a noncompetitive inhibitor of the enzyme complex with respect to its substrate. Dixon plot analysis of the data reveals that the $K_i$ for the $\alpha_N$ peptide inhibition of the GST-Cdk5.GST-Nck5a complex is approximately 25 μM (FIG. 6B). Linearity of the Dixon plots indicates that the $\alpha_N$ peptide is a dead end inhibitor (i.e. the kinase-inhibitor complex is catalytically inactive) (31). This notion is further supported by the near complete inhibition of the kinase by an excess amount (i.e. 400 μM) of the $\alpha_N$ peptide (data not shown).

Structure of the $\alpha_N$ Peptide Determined by CD and NMR—In order to understand the structural basis of Cdk5 and Cdk2 inhibition by the $\alpha_N$ peptide, we determined the structure of the peptide by NMR spectroscopy. The $^1$H NMR spectra of the $\alpha_N$ peptide in aqueous solution showed reasonable chemical shift dispersion (data not shown). However, careful inspection of the spectra revealed that the majority of resonance in both the amide and aliphatic regions had exceptionally broad line widths for a peptide of only 28 amino acid residues. These results indicated that the peptide might be in equilibrium between multiple conformers or in an aggregated stage. A number of amide protons throughout the peptide displayed more than one cross-peak to their α protons in a TOCSY spectrum of the peptide in 90% $H_2O$, 10% $D_2O$, pH 4.0, at 30° C. (data not shown). When the pH of the sample was raised to 4.5 or above, the line widths of the NMR signals broadened further, and the TOCSY spectra were more complicated. Changing the sample temperature (from 8 to 35° C.) or concentration (from 0.5 to 3.5 mM) did not improve the quality of the NMR spectra. CD studies also showed that the molar ellipticity of the peptide at 22 nm remained constant when the concentration of the peptide was varied from 8 μm to 0.2 mM (data not shown). These results indicated that the $α_N$ peptide in aqueous solution has multiple conformational states that are exchanging at slow to intermediate rates. Such multi-conformational equilibrium prevented us from a detailed structural characterization of the peptide in aqueous solution, although we were still able to obtain nearly complete backbone assignment of the peptide at pH 4, 35° C.

Figure 7:
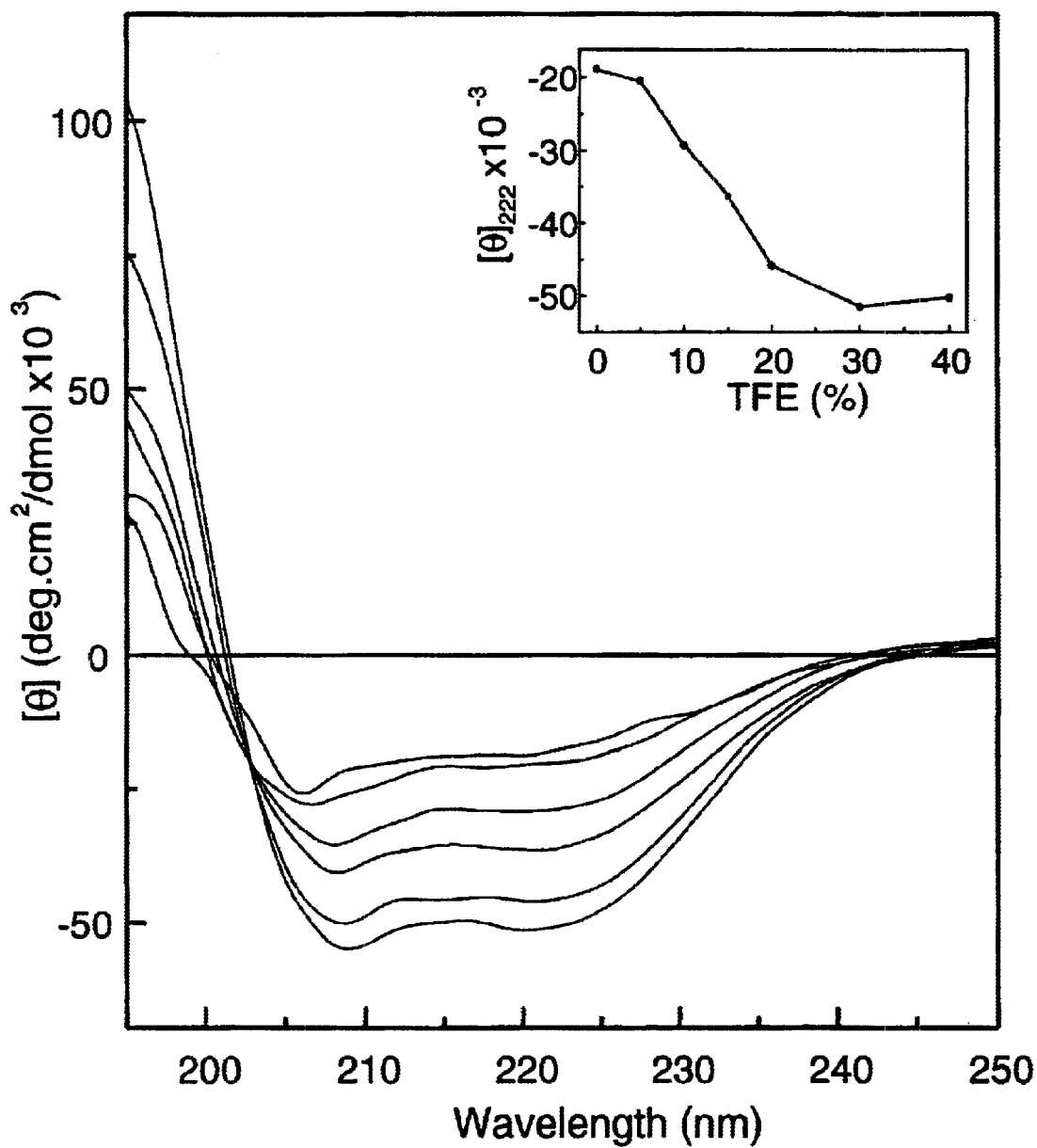

To overcome the complications encountered in aqueous solution, we used TFE as a co-solvent for the structural characterization of the peptide. FIG. 7 shows CD spectra of the $α_N$ peptide at various concentrations of TFE. The CD spectrum of the peptide in the absence of TFE did not show the well defined double minima at 222 and 208 nm which are characteristics of an ordered α-helix in aqueous solution. However, the shape of the CD curve does suggest a measurable population of α-helix. For the samples dissolved in 5, 10, 15, 20, and 30% (v/v) TFE/$H_2O$ mixtures, the CD spectra showed increasingly clearer double minima at 222 and 208 nm, indicating an increasing amount of ordered α-helix. The CD spectra of the peptide in 5 to 30% TFE (v/v) solution had a common intersection at 204 nm, indicating that the peptide was undergoing a two-state conformational transition (FIG. 7), whereas the CD curve of the peptide in aqueous solution did not join this intersection (FIG. 7). This result further supports the suggestion that the peptide in aqueous solution adopts multiconformational states. The structural transition induced by TFE was effectively complete at a TFE concentration of 30% (v/v). Consequently, detailed structural characterization of the $α_N$ peptide was carried out at a TFE concentration of 30%.

Figure 8:
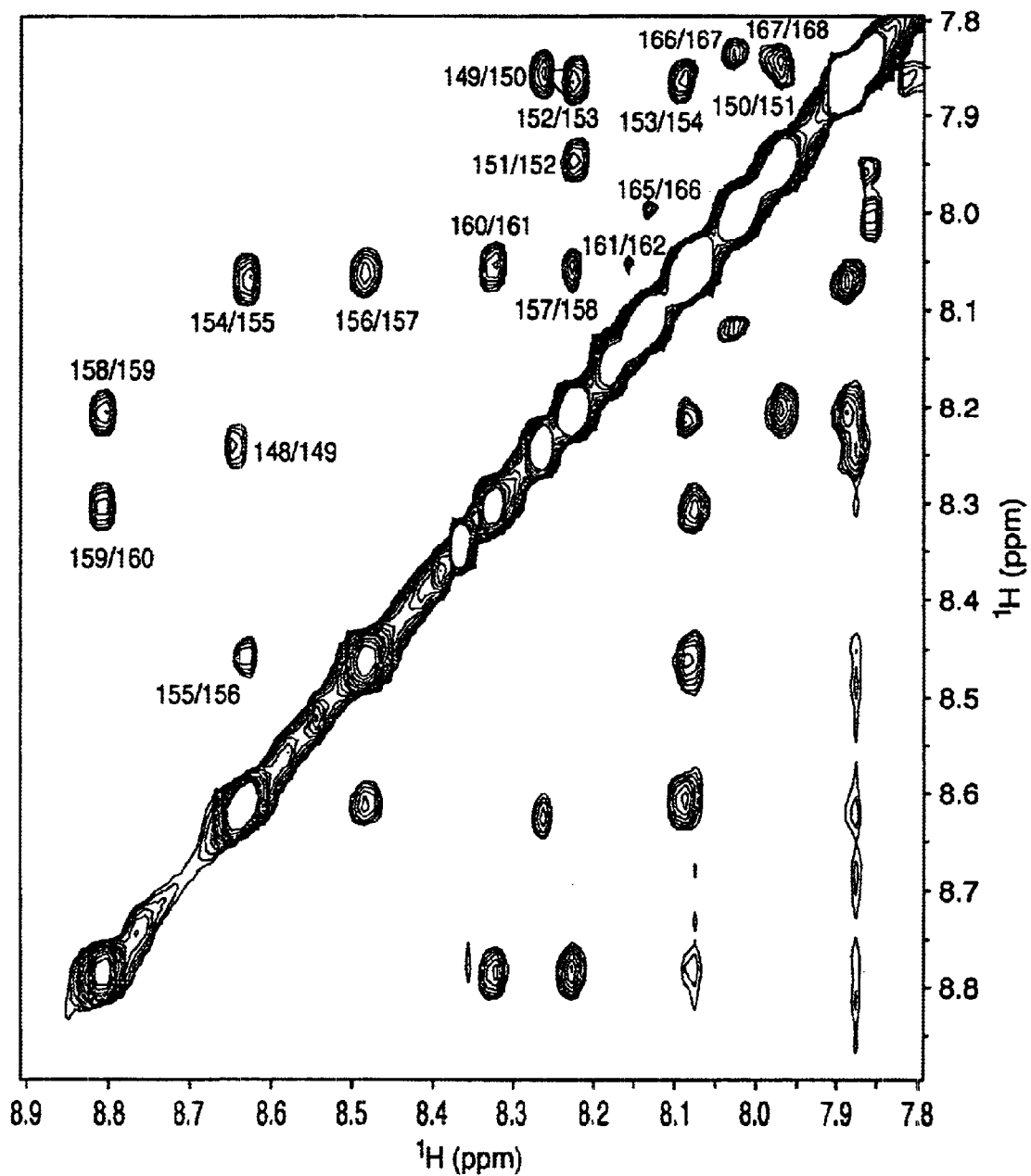
Figure 9:
Figure 10:
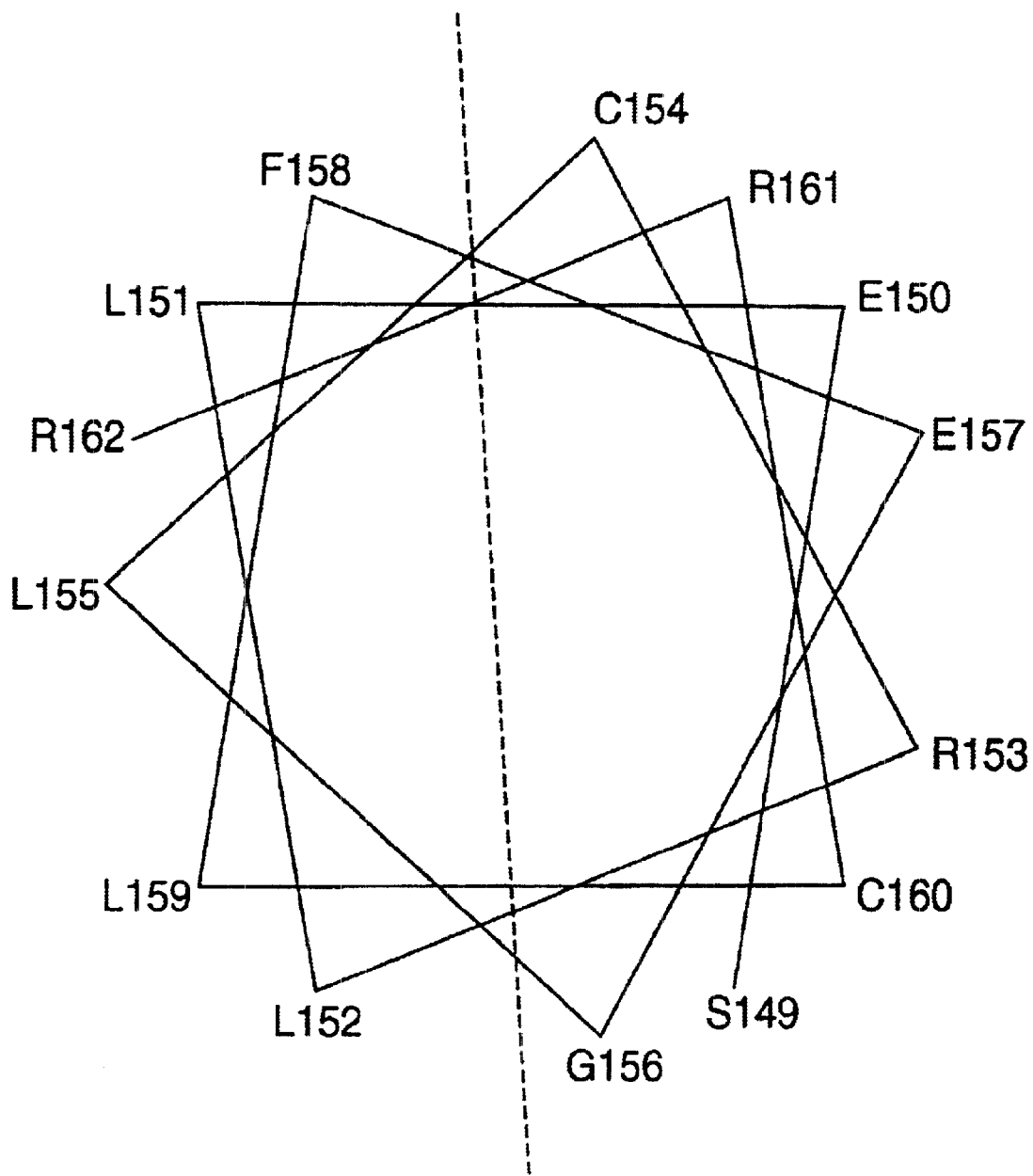

The complete assignment of the $α_N$ peptide in 30% TFE (pH 4.0, 35° C.) was achieved using standard two-dimensional $^1$H NMR techniques (24). FIG. 8 shows the amide-amide region of the NOESY spectrum of the $α_N$ peptide in 30% TFE. A number of well resolved, intense $d_{NN}$ cross-peaks throughout the residues Thr$^{148}$ to Arg$^{162}$ were observed, suggesting the existence of α-helical structure within this stretch of the peptide. FIG. 9 summarizes some of the NOE connectivities observed for the $α_N$ peptide in 30% TFE. The data were extracted from a number of NOESY spectra of the peptide (SEQ ID NO: 1) recorded both in $D_2O$/TFE and $H_2O$/TFE mixtures. Measured αH chemical shifts (presented as the chemical shift index are also included (FIG. 9). Based on the data in FIG. 9, we conclude that the $α_N$ peptide adopts an α-helical. structure from Ser$^{149}$ to Arg$^{162}$. The location of the α-helix of the peptide was determined based on two criteria: (i) the upshifted αH chemical shifts (chemical shift index value of −1), and (ii) a number of intense $d_{NN}$ connectivities and continuous medium range NOEs ($d_{αN}$(i, i+3) and $d_{αβ}$(i, i+3)). FIG. 10 is a helical wheel presentation of the α-helical region of the $α_N$ peptide. It is obvious that the α-helix of the $α_N$ peptide is highly amphipathic with the hydrophobic face consisting of 1 Phe and 4 Leu residues. Nearly identical $d_{NN}$ cross-peaks, albeit with lower intensity, were also observed in the NOESY spectrum of the peptide in aqueous solution under the same pH at room temperature (data not shown), suggesting that the same α-helical structure also exists. The population and stability of such α-helical conformation is, however, significantly lower in aqueous solution than in the presence of TFE.

The minimal activation domain of Nck5a has previously been mapped to contain 142 amino acid residues spanning residues Asp$^{150}$ to Asn$^{291}$. A number of theoretical and experimental studies have suggested that this minimal activation domain of Nck5a adopts a cyclin-fold. In this work, we have identified a 28-residue peptide, residues Ala$^{146}$ to Asp$^{173}$ of Nck5a, that can inhibit the kinase activities of the Cdk5.Nck5a and Cdk2.cyclinA complexes. Based on our earlier prediction, the sequence of this peptide encompasses the N-terminal α-helix of the cyclin fold (thus the peptide is termed the $α_N$ peptide) as well as some flanking amino acid residues at both ends of the helix. The inhibition of Cdk5 by the $α_N$ peptide supports an earlier study that a 50-amino acid fragment spanning residues 109 to 159 of Nck5a retains partial binding capability to Cdk5. Knowing that Nck5a only weakly activates Cdk2 to the basal level, i.e. the activity observed for a Cdk2.cyclin A activity with an even higher potency than in the case with Cdk5.Nck5a inhibition (FIG. 3). In contrast, the corresponding peptide encompassing the N-terminal α-helix of cyclin A inhibits neither Cdk2 nor Cdk5 (FIG. 3). In this work, we have investigated the inhibition of Cdk5 and Cdk2 by the $α_N$ peptide, and it would be interesting to know whether the $α_N$ peptide can also inhibit other members of the Cdk family. Further work is in progress on this matter in our laboratories.

Figure 6:
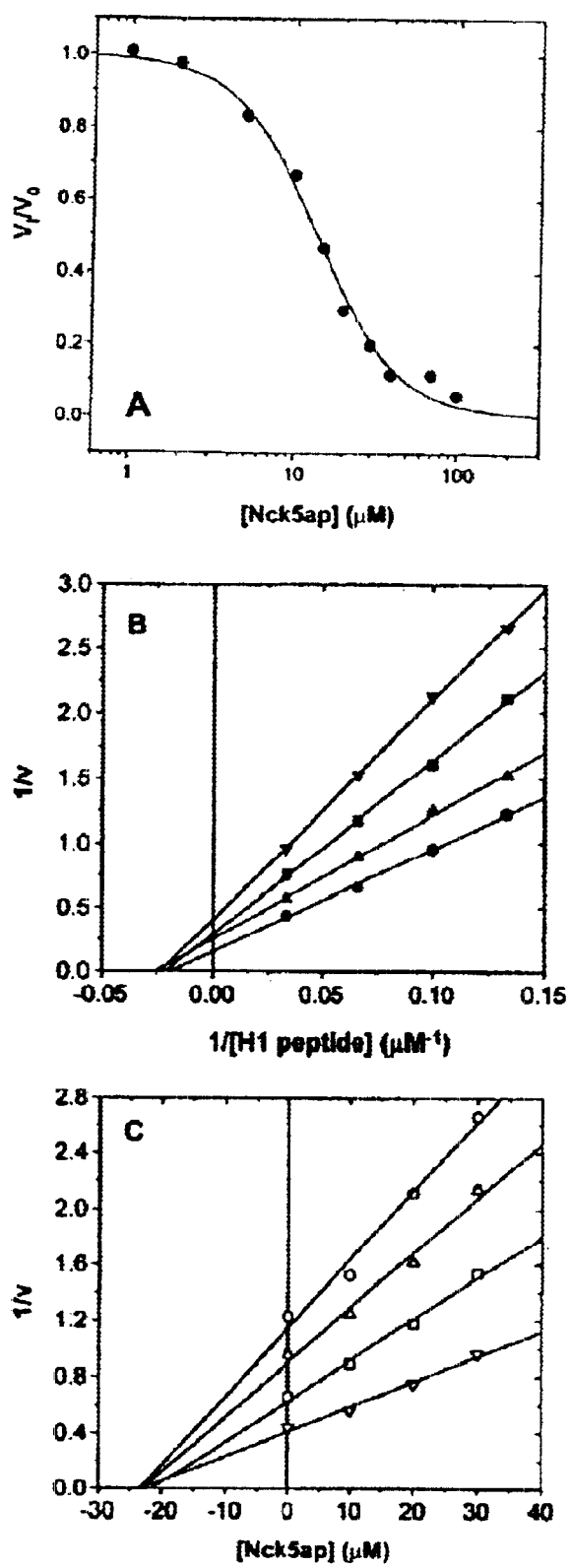

Since the $α_N$ peptide was derived from an internal fragment of Nck5a, it is expected that it might act as a noncompetitive inhibitor with respect to the substrate of Cdk5 (FIG. 6). However, it is unusual that the $α_N$ peptide also functions as a noncompetitive inhibitor with respect to Nck5a (FIGS. 4 and 5). Our results indicate that the inhibition of Cdk5 by the $α_N$ peptide results from the formation of a ternary complex between the $α_N$ peptide and the Cdk5.Nck5a complex. Presumably, the $α_N$ peptide competes with the corresponding fragment in Nck5a for Cdk5 binding. This suggestion is in agreement with an earlier observation that the removal of 4 amino acid residues from the helical part of the peptide fragment from Nck5a completely abolished the ability of Nck5a to activate Cdk5. Comparison of the crystal structures of cyclin A in complex with Cdk2, and cyclin H, has indicated that the N-terminal helix of various cyclins may function as a relatively independent structural unit with respect to the tightly packed cyclin folds. However, this N-terminal helix is indispensable for the activity of cyclins, although the contacts between the helix and the kinase are not extensive. Therefore, we hypothesize that the binding of the $α_N$ peptide dislodges the corresponding N-terminal α-helix of Nck5a from Cdk5, thereby inhibiting the activity of the enzyme. The dislocation of the N-terminal α-helix does not lead to dissociation of the whole activator. Unlike the $α_N$ peptide, the control peptide derived from cyclin A inhibits neither Cdk2.cyclin A nor Cdk5.Nck5a (FIG. 3), suggesting a significant difference between the binding and activation of Cdk2 by cyclin A, on the one hand, and Cdk5 by Nck5a, on the other.

The α-helical structure detected by CD spectroscopy for the $α_N$ peptide in aqueous solution (FIG. 6) qualitatively agrees with our earlier prediction that part of the $α_N$ peptide could adopt an α-helical conformation. The existence of multiconformational states of the peptide prevented us from a detailed structural determination of the peptide in aqueous solution. Hence, TFE and water were used as a co-solvent to study the structure of the $\alpha_N$ peptide. The peptide segment from Ser$^{149}$ to Arg$^{162}$ was found to adopt a stable α-helical conformation in aqueous TFE solution. Similar NOE patterns (especially d$_{NN}$ NOE connectivities that were relatively well resolved) have also been observed for the $\alpha_N$ peptide in pure water solution (data not shown), suggesting that the same α-helical conformation exists in this solution. It has been observed in numerous cases that TFE can either stabilize unordered α-helices in various peptide fragments in aqueous solution or promote the formation of α-helices in peptide fragments that have intrinsic propensities to form α-helix, but not induce new α-helical conformation. Therefore, we suggest that the α-helical region observed in the $\alpha_N$ peptide would probably adopt a similar α-helical structure in Nck5a. The peptide region found to adopt an α-helical conformation has also been predicted to be an α-helix in the protein, and this α-helix aligns well with the N-terminal α-helix of the first cyclin-fold of cyclin A (FIG. 1). The above notion is further underscored by the fact that the same α-helical structure was observed for the cyclin A peptide in solution as the corresponding N-terminal helix in the full-length cyclin A structures.

A helical wheel presentation of the α-helix found in the $\alpha_N$ peptide shows that the peptide is amphipathic with 4 Leu and 1 Phe on the hydrophobic face (FIG. 10). Indeed, deletion of part of the N-terminal end of the α-helix completely abolished the inhibitory effect of the peptide. In an earlier study, we have also shown that mutations of the hydrophobic amino acid residues in the α-helix (Leu$^{151}$, Leu$^{152}$) to a polar amino acid residue (Asn) greatly reduced the Cdk5 activation ability of Nck5a. In the crystal structure of the Cdk2.cyclin A complex, the corresponding N-terminal α-helix of cyclin A makes a significant amount of contacts with various regions (e.g. T-loop and α3 helix) of Cdk2 via hydrophobic interactions (Brown, N.R, 1995). It is likely that the hydrophobic face of the peptide forms the major binding area between the $\alpha_N$ peptide and Cdks. This hypothesis was supported by the result shown in FIG. 3 that an unrelated amphipathic MLCK peptide was able to inhibit both Cdk5 and Cdk2. Like the $\alpha_N$ peptide, the α-helical structure of the MLCK peptide in solution can be promoted by TFE, and the MLCK peptide binds to calmodulin in an α-helical conformation with its hydrophobic face forming the main contact area with calmodulin. The lower extent and potency of inhibitory activity observed with the MLCK peptide may originate from a large sequence difference in the α-helical region as well as the C-terminal random coil region between the MLCK peptide and the $\alpha_N$ peptide.

The structure of the $\alpha_N$ peptide determined here and the interaction observed between the N-terminal the α-helix of cyclin A and Cdk2 suggest that systematic alterations of the amino acid residues in the hydrophobic face of the the α-helix and the C-terminal end of the $\alpha_N$ peptide may enable us to find peptide inhibitors with higher specificity and/or potency toward various Cdks. We note that the present Cdk5 inhibitory peptide was discovered based on the unique regulatory property of the enzyme by its activator. It is, therefore, promising to develop the peptide into a Cdk5 specific inhibitor in contrast to the majority of ATP analog derived compounds, which acts as general kinase inhibitors. Also, the peptide in its present form can be used to screen for chemical compounds that can inhibit the activity of the Cdk5.Nck5a complex.

Thus, the present invention has demonstrated that the internal fragment of Nck5a of 28-residue peptide encompassing amino acid residues Gln 145 to Asp 173 has a specific and efficient regulatory function towards Cdk5 and Cdk2. The invention as described is deemed to incorporate equivalents to the integers recited where such equivalents would be apparent to those skilled in the art. The description is provided by way of examples and experiments and is not to be considered limited to the scope of the invention which is defined in the appended.

What is claimed is:

1. An inhibitory peptide derived from a neuronal-derived cyclin-dependent kinase 5 activator (Nck5a) for the activation of the cyclin-dependent-kinase 5(Cdk5) wherein said inhibitory peptide consists of the twenty-eight amino acid residues Ala$^{146}$ to Asp$^{173}$ of Nck5a having the complete amino acid sequence "ASTSELLRCLGEFLCRRCYR-LKHLSPTD" (SEQ ID NO: 1), and wherein said inhibitory peptide is capable of inhibiting the kinase activities of Cdk5.

2. An inhibitory peptide according to claim 1 wherein said peptide acts as a non-competitive inhibitor of said Cdk-5 and Nck5a complex and wherein said peptide adopts an amphipathic alpha-helical secondary structure corresponding to amino acids Ser$^{149}$ to Arg$^{162}$ of NcK5a and having the complete amino acid sequence "SELLRCLGEFLCRRCY" (SEQ ID NO:20).

3. An inhibitory peptide as claimed in claim 1, wherein said inhibitory peptide is capable of specifically and efficiently inhibiting said Cdk5 and Nck5a complex.

4. An inhibitory peptide derived from a Nck5a for the activation of Cdk5, wherein said inhibitory peptide:
   a) is a peptide 28 amino acids long comprising amino acid sequence SELLRCLGEFLCRRCY (SEQ ID NO:2), and b) adopts an amphipathic alpha-helical secondary structure, and wherein said secondary structure of said inhibitory peptide substantially corresponds to the secondary structure of amino acid sequence $Ser^{149}$ to $Arg^{162}$ of Nck5a.

5. An inhibitory peptide as claimed in claim 4, wherein each of the amino acid residues of said inhibitory peptide which corresponds to the amino acid residues of Nck5a at positions 151, 152, 155, and 159 is a Leu residue, and the amino acid residue of said inhibitory peptide which corresponds to the amino acid residue of Nck5a at position 158 is a Phe residue.

* * * * *

SEQUENCE LISTING

```
<160> NUMBER OF SEQ ID NOS: 5

<210> SEQ ID NO 1
<211> LENGTH: 28
<212> TYPE: PRT
<213> ORGANISM: Homo sapiens

<400> SEQUENCE: 1

Ala Ser Thr Ser Glu Leu Leu Arg Cys Leu Gly Glu Phe Leu Cys Arg
 1               5                  10                  15

Arg Cys Tyr Arg Leu Lys His Leu Ser Pro Thr Asp
            20                  25

<210> SEQ ID NO 2
<211> LENGTH: 16
<212> TYPE: PRT
<213> ORGANISM: Homo sapiens

<400> SEQUENCE: 2

Ser Glu Leu Leu Arg Cys Leu Gly Glu Phe Leu Cys Arg Arg Cys Tyr
 1               5                  10                  15
```

```
<210> SEQ ID NO 3
<211> LENGTH: 142
<212> TYPE: PRT
<213> ORGANISM: Homo sapiens

<400> SEQUENCE: 3

Glu Leu Leu Arg Cys Leu Gly Glu Phe Leu Cys Arg Arg Cys Tyr Arg
 1               5                  10                  15

Leu Lys His Leu Ser Pro Thr Asp Pro Val Leu Trp Leu Arg Ser Val
            20                  25                  30

Asp Arg Ser Leu Leu Leu Gln Gly Trp Gln Asp Gln Phe Ile Thr Pro
        35                  40                  45

Ala Asn Val Val Phe Leu Tyr Met Leu Cys Arg Asp Val Ile Ser Ser
    50                  55                  60

Glu Val Gly Ser Asp His Glu Leu Gln Ala Val Leu Leu Thr Cys Leu
65                  70                  75                  80

Tyr Leu Ser Tyr Ser Tyr Met Gly Asn Glu Ile Ser Tyr Pro Leu Lys
                85                  90                  95

Pro Phe Leu Val Glu Ser Cys Lys Glu Ala Phe Trp Asp Arg Cys Leu
            100                 105                 110

Ser Val Ile Asn Leu Met Ser Ser Lys Met Leu Gln Ile Asn Ala Asp
        115                 120                 125

Pro His Tyr Phe Thr Gln Val Phe Ser Asp Leu Lys Asn Glu
    130                 135                 140

<210> SEQ ID NO 4
<211> LENGTH: 31
<212> TYPE: PRT
<213> ORGANISM: Homo sapiens

<400> SEQUENCE: 4

Asp Tyr His Glu Asp Ile His Thr Tyr Leu Arg Glu Met Glu Val Lys
 1               5                  10                  15

Cys Lys Pro Lys Val Gly Tyr Met Lys Lys Gln Pro Asp Ile Thr
            20                  25                  30

<210> SEQ ID NO 5
<211> LENGTH: 31
<212> TYPE: PRT
<213> ORGANISM: Homo sapiens

<400> SEQUENCE: 5

Asp Tyr His Glu Asp Ile His Thr Tyr Leu Arg Glu Met Glu Val Lys
 1               5                  10                  15

Pro Lys Pro Lys Val Gly Tyr Met Lys Lys Gln Pro Asp Ile Thr
            20                  25                  30
```